United States Patent [19]
Israelachvili

[11] Patent Number: 5,861,954
[45] Date of Patent: Jan. 19, 1999

[54] INSTRUMENT FOR MEASURING STATIC AND DYNAMIC FORCES BETWEEN SURFACES IN THREE DIMENSIONS

[76] Inventor: Jacob N. Israelachvili, 2233 Foothill La., Santa Barbara, Calif. 93105

[21] Appl. No.: 728,465

[22] Filed: Oct. 10, 1996

[51] Int. Cl.[6] .............................. G01L 1/00; G01N 13/00; G01B 9/02; G01B 11/16
[52] U.S. Cl. ....................................... 356/356; 73/862.632
[58] Field of Search .................... 356/356, 373, 356/374; 73/812.381, 862.632

[56] References Cited

U.S. PATENT DOCUMENTS

| | | | |
|---|---|---|---|
| 3,796,494 | 3/1974 | Takabayashi | 356/358 |
| 3,870,414 | 3/1975 | Duffy | 356/356 X |
| 4,050,818 | 9/1977 | Sharpe, Jr. et al. | 356/356 X |
| 5,164,791 | 11/1992 | Aubo et al. | 356/356 |
| 5,193,383 | 3/1993 | Burnham et al. | 250/307 X |
| 5,572,233 | 11/1996 | Kuda et al. | 356/356 |

*Primary Examiner*—Thomas P. Noland
*Attorney, Agent, or Firm*—The Kline Law Firm

[57] ABSTRACT

A surface forces measuring apparatus (SFA) including miniature rheometers and friction measuring devices. Both static (i.e., equilibrium) forces and dynamic (e.g., time-dependent such as viscous, hysteretic and frictional) forces can be measured between two surfaces in relative motion to each other along the z-direction (normally) or the x- or y-directions (horizontally), or along any desired direction in 3D space. The new instrument uses a novel combination of piezoelectric tubes and N-type bimorphs, and a three-stage mechanical mechanism to produce linear motion of one of the surfaces along any desired direction, and a combination of an optical technique and semi-conductor strain-gauges allows for the force produced on the other surface to be directly measured, also in any direction (which may be in a different direction from that of the first surface which generates the force). Force measuring sensitivity is significantly higher, both in magnitude and time-response, than in previous force-measuring devices, particularly in the x- and y-directions, enabling weaker forces and rapid transient effects to be studied in detail.

10 Claims, 14 Drawing Sheets

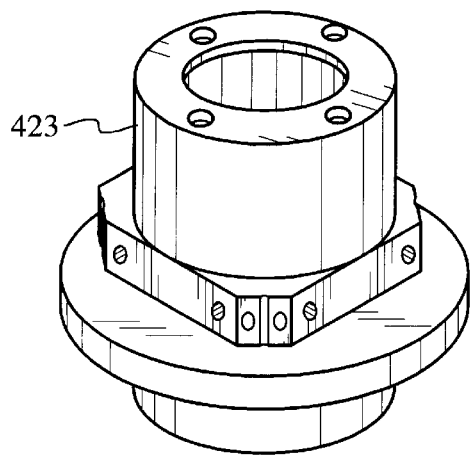
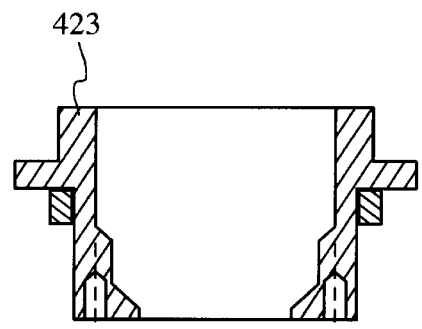
FIG. 11A    FIG. 11B
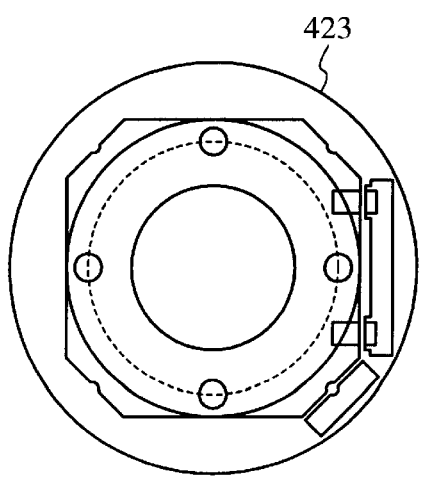
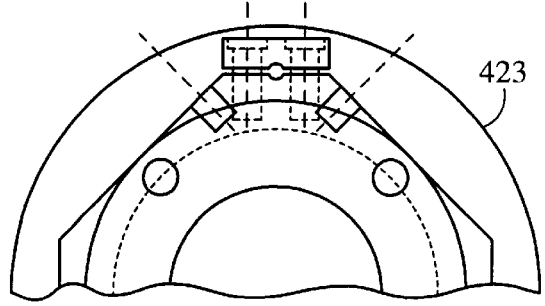
FIG. 11C    FIG. 11D

INSTRUMENT FOR MEASURING STATIC AND DYNAMIC FORCES BETWEEN SURFACES IN THREE DIMENSIONS

FIELD OF THE INVENTION

This invention relates to broad areas of surface science and engineering requiring measurements or knowledge of the various intermolecular forces operating between surfaces when they approach each other. The surfaces may be at rest (static or equilibrium forces) or in motion (dynamic or viscous forces), and they may be exposed to vacuum, a vapor atmosphere, or totally immersed in a liquid.

BACKGROUND OF THE INVENTION

DESCRIPTION OF THE PRIOR ART

Historical developments of Surface Forces Apparatuses (SFA's)

Surface forces apparatuses (SFA's) are instruments that measure the forces between surfaces. They have been in existence since the mid-1950's. Until the 1970's, SFA's measured the forces between two surfaces in air or in vacuum. Gradual improvements in surface sample preparation (e.g., producing smoother surfaces) and in distance-measuring techniques resulted in a series of improved SFA's, and today these can measure the normal force between two macroscopic surfaces (force accuracy: approx. $10^{-8}$N) as a function of surface separation (distance accuracy: approx. 1 Å). Forces are generally obtained by measuring the deflection of a cantilever spring using an optical or electrical position-sensitive measuring technique, and the separation between the two interacting surfaces, as well as their shape, is measured with a standard optical technique that uses multiple beam interference fringes (known as "FECO"≡"Fringes of Equal Chromatic Order").

In 1969 Tabor & Winterton and later Israelachvili & Tabor developed Surface Forces Apparatuses (SFA's), initially for measuring the van der Waals forces between surfaces in air or vacuum. In 1976, Israelachvili & Adams designed the first apparatus (later known as SFA Mk I) for measuring forces between surfaces in liquids and controlled vapor atmospheres, allowing control and measurement of the surface separation to within 0.1 nm. The SFA Mk 1, and later versions (SFA Mks 2, 3 and 4), enabled the first direct and detailed measurements to be made of the fundamental forces between surfaces in vapors and liquids. Subsequent models, such as SFA Mk 2, SFA 3, SFA Mk 4, and other versions, were essentially incremental improvements on earlier models without introducing new qualitative features.

Current SFA technology—principles of SFA operation : The principles on which current SFA's operate are simple: one of the surfaces (usually the upper) is rigidly mounted at the end of a piezoelectric crystal tube while the lower surface, which faces the upper, is suspended at the end of a cantilever spring system (the force-measuring spring). The surfaces can be moved towards or away from each other using a two to four-stage system of mechanical and piezo controls of increasing accuracy, and an optical technique using FECO fringes is used to measure the separation between the surfaces to ±0.1 nm. The force between two surfaces is measured by moving the two surfaces towards or away from each other using one of the above controls, and simultaneously measuring the deflection of the force-measuring spring using the optical FECO technique. This gives the force at any particular surface separation.

The principles used in making direct force measurements are usually very simple, the main challenge has always been in the design of a mechanical device that would successfully apply these principles at the angstrom level.

FIG. 1 shows one of the more advanced basic SFA's, known as SFA 3, designed and used in the laboratory of the inventor at the University of California at Santa Barbara. This SFA will now be described in detail since one of its features—the movement/positioning of the lower surface in the z-direction—is also used in the present invention.

FIG. 1 shows a section through SFA 3. There are four distance controls: normal micrometer (M1), differential micrometer (M2), differential spring control (M3), and piezoelectric tube. The lower surface is mounted at the end of a variable-stiffness double-cantilever force-measuring spring (S) which is connected via the spring mount to the distance controls of the upper (control) chamber via a teflon bellows (B). The wheel and shaft are used for laterally moving the spring clamp and thereby changing the stiffness of the force-measuring spring. The lower chamber is bolted to the underside of the upper chamber from which it is completely sealed by the bellows, as well as being sealed from the outside with teflon O-rings. The main translation stage unit (T) has 4 double-cantilever springs machined out of a single Copper-Beryllium block. This part ensures that the two surfaces move vertically and perfectly linearly relative to each other with no displacement or rotation in any other direction. The main part of the translation stage is bolted to the inside of the control chamber. The second part is bolted to a single-cantilever spring which acts differentially to the helical spring when the differential micrometer M3 is rotated. All springs parts are machined from Cu—Be alloy before they are hardened by heat treated (tempered).

Forces are measured between the two mica or mica coated surfaces supported on two cylindrical silica disks. The upper disk is attached to the piezoelectric PZT-5A crystal tube which is mounted on a support that can be moved laterally and rotated before it is clamped tightly to the top of the apparatus. The apparatus has two separate parts, an upper (control) chamber, and a lower (bathing) chamber. The control chamber handles the four distance controls, the force-measuring spring adjustment, and the positioning and clamping of the two surfaces. Its workings are totally sealed from the lower chamber via the Teflon bellows B. The lower chamber acts as a simple bath that can be bolted underneath the upper chamber and then filled with liquid. It is thus completely sealed both from the outside environment as well as from the mechanical controls of the upper chamber. The lower and upper chambers are made of 316 stainless steel. The lower chamber can also be made of PTFE or some other inert material such as Kel-F. It is easy to clean and can be readily replaced by another bathing chamber. At no point during or between experiments does the control chamber have to be opened or dismantled; indeed, once the control chamber has been assembled it requires no further attention.

The four distance controls of the SFA 3 include three mechanical controls and one piezoelectric control. The three mechanical controls are based on a multiple spring translation assembly, located roughly at the center of the upper (control) chamber. The main part of this assembly is the vertical-motion translation stage, machined from a single block of Cu—Be alloy and consisting of four equal double-cantilever spring systems. This type of design ensures perfectly linear motion, with no possible movement in any other direction. The eight cantilever springs of this unit also ensure that there is no possibility of any wobble or rotation, or any other type of unwanted movement, friction or backlash as occurs with dove-tailed slides or screw-thread drives. To further ensure that there is also no "buckling" of the springs, the vertical force that induces displacement of the 8-spring unit is applied through an axis that passes through the center of the unit.

The full translation spring assembly includes a single cantilever spring that is bolted to the translation stage and whose center also passes through the center of the 8-cantilever spring unit. The assembled unit of these two parts (T) fits inside the control chamber via four bolts. At the bottom of this unit there is a threaded hole to which are attached the PTFE bellows (B) and the force-measuring spring mount. The spring mount protrudes into the lower chamber, and the bellows isolates the two chambers from each other.

Control of Surface Separation to 1 Å: There are three mechanical distance controls (two coarse and one medium) and one piezoelectric (fine) control having the following resolution and workable range. Coarse control: normal micrometer M1 (500 nm over a range of 6 mm); Medium control: differential micrometer M2 (50 nm over a range of 0.1 mm); Fine control: differential spring operated by micrometer M3 (1 nm over a range of 5 mm); and Piezo control: piezoelectric tube (<0.1 nm over a range of 1 $\mu$m). The spindle of micrometer M1 and M2 presses against the 8-spring unit T via the short single-cantilever spring that is in series with that unit. When the spindle of micrometer M3 moves a distance D, it compresses a helical spring by this amount which in turn presses against the single-cantilever spring on unit T via the lever arm. The resulting vertical movement of unit T (and the spring mount) is therefore determined by the ratio of the stiffness of these two springs which, being 1,000:1, effectively gears down the motion of the lower surface by a factor of 1,000, viz. from D to D/1,000. The three micrometer controls can be operated manually or by variable-speed DC motors.

Measuring distances and surface profiles using the FECO technique: Surface separations and profiles can be measured to within about 1 Å (0.1 nm) by monitoring the movement of multiple beam interference fringes. This technique is known as "FECO", for "Fringes of Equal Chromatic Order". These sharp interference fringes are produced when a beam of white light is made to pass through the two mica sheets (FIG. 1). The transparent mica sheets are of equal thickness (about 1–3 $\mu$m thick) and are each coated with a highly reflecting layer of silver (thickness ~550 Å) before they are glued, silvered sides down, onto the cylindrically curved silica discs. The interference fringes are produced by multiple reflections of light between the two silvered layers, so that only certain wavelengths (those that interfere constructively) emerge from the other side of the sheets. The emerging beam is focussed onto the slit of a normal grating spectrometer which separates out the different colors (interference fringes). Depending on the shapes of the two surfaces these fringes appear as sharp lines or curves at the exit window of the spectrometer where they can be viewed by eye through a normal microscope eyepiece or recorded on film or a video camera.

From the positions and shapes of the FECO fringes one can determine not only the surface separation but also their shapes and the refractive index of the medium between them. Equations describing how one translates the measured wavelengths to surface separations and refractive indices have been described by Israelachvili and others.

Measuring Forces: Given the facility for moving the surfaces towards or away from each other and independently measuring their separation, each with a sensitivity or resolution of 1 Å, the force measurements themselves now become straightforward. The force is measured by expanding or contracting the piezoelectric crystal by a known amount and then measuring optically how much the two surfaces have actually moved. Any difference in the two values when multiplied by the stiffness of the force-measuring spring gives the force difference between the initial and final positions. In this way, by starting at some large separation where there is no detectable force and working systematically towards smaller separations both repulsive and attractive forces can be measured with a sensitivity of about $10^{-6}$ g ($10^{-8}$N) and a full force-law can be obtained over any distance regime.

Advantages of the FECO technique over other distance-measuring techniques: There are two critical reasons for why the FECO technique is the only one capable of unambiguously measuring surface separations and inter-surface force-laws (force versus surface separation). The first is that the surface separation is measured at the point of closest approach of the two surfaces, i.e., the separation is measured exactly where one wants to know it. All other force-measuring techniques (whether capacitance, optical, electric or magnetic) do not measure the surface separation, that is, the distance between two surfaces, but the displacement of a single spring or balance arm at some point away from the interaction zone. From this displacement the separation is then inferred. In this way any elastic deformations of the surfaces occurring around the contact zone become mixed in with, and inseparable from, the measured force-displacement curves. With the FECO method, the distances between the two surfaces and any deformations of the materials are unambiguously distinguishable and measurable independently of the forces.

The second advantage of the FECO method is that one can measure the surface shape or profile, and in particular the local radius of curvature R of the two interacting surfaces. This is essential for comparing measured forces with theory or with other experiments.

FIG. 2 shows a sliding attachment (or "Friction device") that was developed in 1988 for use with the SFA Mk 2. This Friction Device allows for the two surfaces to be slid or moved laterally past each other (rather than normally as in conventional force measurements). Sliding motion is initiated via a motor-driven micrometer and the friction force is measured from the deflection of a double-cantilever spring system using resistance strain gauges. With this attachment, sliding speeds in the range 0.01 to 100 $\mu$m/sec can be attained, and lateral (shear or friction) forces can be measured to an accuracy of about $10^{-3}$N.

Limitations of the prior art: The systems and phenomena being called upon for study with SFA technology are rapidly growing in complexity: these now include complex polymeric and lubricant fluid systems, the interactions of biological cell surfaces, dynamic and time-dependent interactions over a large range of time-scales, molecular structure and relaxations at surfaces and in confined liquid films, etc. Such studies require greater versatility in the different types of forces that may be measured than has so far been possible. Thus, they require forces to be measured along different directions (axes), a higher force-measuring sensitivity, a greater dynamic range of measuring times and sliding speeds (from very slow to very fast), improved distance resolution, and higher mechanical stability (requiring the elimination of backlash and thermal drift). A whole generation of new phenomena could be studied if only some of these deficiencies or limitations could be overcome. Our primary aim here was the identification of these limitations, and the design and construction of a new device that overcame these limitations. These limitations will now be described in more detail.

(a) Inability to measure "vectorially" coupled interactions in 3-D. Recent research has indicated that normal forces (in the z-direction) and lateral forces (in the x- and y-directions) are generally "vectorially" coupled, for example, where sliding motion of one surface in the x-direction produces a force on the other surface in the y-direction. Existing SFA's cannot measure vectorially-coupled forces or interactions. More precisely, existing SFA's cannot simultaneously induce and/or measure forces along any desired (arbitrary) direction in three-dimensional space.

(b) Inability to simultaneously measure normal and lateral forces accurately. Existing friction-measuring attachments replace, and therefore cannot be used together with, the sensitive piezoelectric tube supporting the upper surface. Thus, normal forces cannot be induced or measured accurately at the same time as shearing, sliding or friction forces are being measured.

(c) Limited dynamic range of sliding speeds. Recent studies on friction and lubrication have indicated that important changes can occur at different sliding speeds, but that measurements have to be made over a very large range of speeds, extending over 10 decades or more, to fully appreciate these effects. Existing friction-measuring instruments or attachments cannot measure lateral forces over a range greater than about four orders of magnitude.

(d) Inability to measure fast transient effects. Recent studies have shown that important short-lived "transient" effects occur during the interaction of two surfaces, and there is an increasing need for SFA's to be able to measure such rapidly changing, non-equilibrium forces. Existing force-measuring techniques are not geared to measuring rapid changes occurring over time-scales much shorter than 0.1 sec.

(e) Inability to measure slowly changing and true equilibrium forces. The two surfaces are prone to thermal drifts which can greatly diminish the accuracy of the forces measured below the theoretically attainable limit of at least $10^{-8}$N ($10^{-6}$ g). These drifts can usually be minimized by thermostating the apparatus or the experimental room to 0.1° C., but they preclude accurate measurements of forces that take a long time to reach equilibrium. Because of difficulties in controlling thermal drifts, existing SFA's cannot accurately measure forces that slowly change with time or forces that take a very long time to stabilize, for example, time-dependent adhesion forces, hysteretic forces, hydrodynamic interactions, etc. Thus, forces and interactions that require more than about 30 minutes to reach equilibrium cannot be reliably accessed by the prior art.

(f) Limited interfacing capabilities, expandability and upgradability. Existing SFA's are not designed for interfacing with other commonly used experimental techniques, such as light scattering or fluorescence microscopy techniques, nor are they easily adaptable for incorporating new attachments that can expand their versatility and scope.

(g) Limited accuracy in measuring normal forces. Currently the detection limit in measurements of normal forces is about $10^{-8}$N. This is acceptable for most applications, but does not allow certain weak, but nevertheless important, forces to be measured.

(h) Limited accuracy in measuring lateral forces. Currently the detection limit in measurements of lateral forces is about $10^{-3}$N. This is fairly crude and precludes measurements of any but the strongest friction forces.

(i) Limited accuracy in measuring lateral deflections. Currently the detection limit in measurements of lateral distances is about 500 Å. This precludes measurements of any friction phenomena occurring or varying on the molecular scale.

SUMMARY, OBJECTS, AND ADVANTAGES OF THE INVENTION

In summary, the present invention is a surface forces measuring apparatus (SFA) including miniature rheometers, and friction measuring devices. Both static (i.e., equilibrium) forces and dynamic (e.g., time-dependent such as viscous, hysteretic and frictional) forces can be measured between two surfaces in relative motion to each other along the z-direction (normally) or the x- or y-directions (horizontally), or along any desired direction in 3D space. The new instrument uses a novel combination of piezoelectric tubes and N-type bimorphs, and a three-stage mechanical mechanism to produce linear motion of one of the surfaces along any desired direction, and a combination of an optical technique and semi-conductor strain-gauges allows for the force produced on the other surface to be directly measured, also in any direction (which may be in a different direction from that of the first surface which generates the force). Force measuring sensitivity is significantly higher, both in magnitude and time-response, than in previous force-measuring devices, particularly in the x- and y-directions, enabling weaker forces and rapid transient effects to be studied in detail.

Several objects and advantages of this invention are:

(a) Ability to measure vectorially coupled interactions in 3-D. The main object of this invention is to provide a multi-purpose force-measuring instrument capable of moving one surface (the driving surface) vectorially along any direction in three-dimensional space (i.e., along any desired x-y-z direction) while simultaneously measuring the static or dynamic force produced in the other (detector) surface and the direction of the induced force (which need not be the same as the direction of motion of the driving surface) and the surface separation and profile.

(b) Ability to simultaneously measure normal and lateral forces accurately. Lateral, shear and friction forces can be measured without sacrificing the highly sensitive piezoelectric positioning-device supporting one of the surfaces.

(c) Increased range of lateral sliding speeds. Sliding speeds can be varied from above 105 $\mu$m/sec to below $10^{-5}$ $\mu$m/sec—a range of 10 decades (orders of magnitude), which is 6 decades more than the prior art.

(d) Increased time-resolution for measuring fast transient effects. By using friction-force measuring springs that are stiffer and shorter, and by drastically reducing the mass (weight) of the platform supporting the upper surface, the natural frequency of vibrations of the friction-force measuring system has been increased by more than an order of magnitude. Thus, transient events shorter than a few milliseconds can now be measured during sliding by recording the output signal from the strain gauges on the friction springs on or storage oscilloscope or other type of data acquisition system. This is a significant increase in response time resolution—by almost two decades—over the prior art.

(e) Ability to measure slowly changing and true equilibrium forces. With the Balance Attachment, forces that may take hours, days or even weeks to equilibrate can now be measured. Additionally, very slow transient effects can also be reliably studied. In principle, the Balance Attachment can measure any equilibrium force or interaction, regardless of how long it takes to equilibrate and regardless of the thermal drifts present. The only limitation here being the patience of the operator.

(f) Improved expandability, upgradability and interfacing capabilities. The new SFA is readily adaptable for incorporating a number of new attachments for further increasing the scope of force measurements. It is also readily adaptable for interfacing with other established laboratory measuring techniques such as X-ray synchrotron reflectivity and scattering experiments, and fluorescence and other optical microscopies.

(g) Increased accuracy in measuring normal forces. With the balance attachment, the accuracy of measuring the normal forces between two surfaces moving towards or away from each other is increased by two orders of magnitude to $10^{-10}$N.

(h) Increased lateral force-measuring sensitivity. By using semi-conducting strain gauges and a friction-force measuring spring of variable stiffness, the accuracy of measuring the shear or friction forces between two surfaces moving laterally relative to each other has been increased by two orders of magnitude to $10^{-5}$N.

(i) Increased accuracy in measuring lateral deflections. The accuracy of measuring the lateral displacement of one surface sliding across another is increased by two orders of magnitude to about 5 Å, which now allows for friction phenomena and transient events to be studied at the molecular level.

(j) Studies with opaque liquids. A facility has been introduced for adjusting the height of the light entrance window. This allows for a great reduction in the liquid volume that the light has to pass through (from cm to microns), thereby enabling opaque liquids to be used in SFA experiments.

(k) Great interfacing capabilities with optical equipment. Enlarged objective port hole and <5 mm optical working distance from surfaces to microscope objective allows for objectives with shorter focal lengths and higher magnifications (up to ×20) to be used as well as certain types of specialized wide-bodied objectives, for example, fluorescence microscope objectives.

(l) Unique features of SFA-FECO experiments: The SFA technique for measuring forces, when used together with the FECO optical technique for visualizing two surfaces, allows for the unambiguous measurements of the following parameters that cannot be independently measured by any other combination of techniques: (i) the static and dynamic forces, both normal and lateral, between the two surfaces, (ii) independent measurement of the separation between the two surfaces at their point of closest approach, (iii) quantitative visualization of the local surface geometry and how it changes, for example, due to force-induced elastic deformations, during sliding or other motions, arid (iv) the ability to visualize contamination and trapped particles between the surfaces from the deformed shapes of the FECO fringes in combination with refractive index measurements.

These and other objects and advantages of the present invention, such as great user-friendliness, will become apparent to those skilled in the art in view of the description of the best presently known mode of carrying out the invention as described herein and as illustrated in the drawings.

BRIEF DESCRIPTION OF THE DRAWINGS

FIG. 3A shows the 2D detector.

FIG. 3B shows the balance assembly.

FIGS. 11A–D are detailed views of the Piezo Mount.

BEST MODE OF CARRYING OUT THE INVENTION

Figure 3:
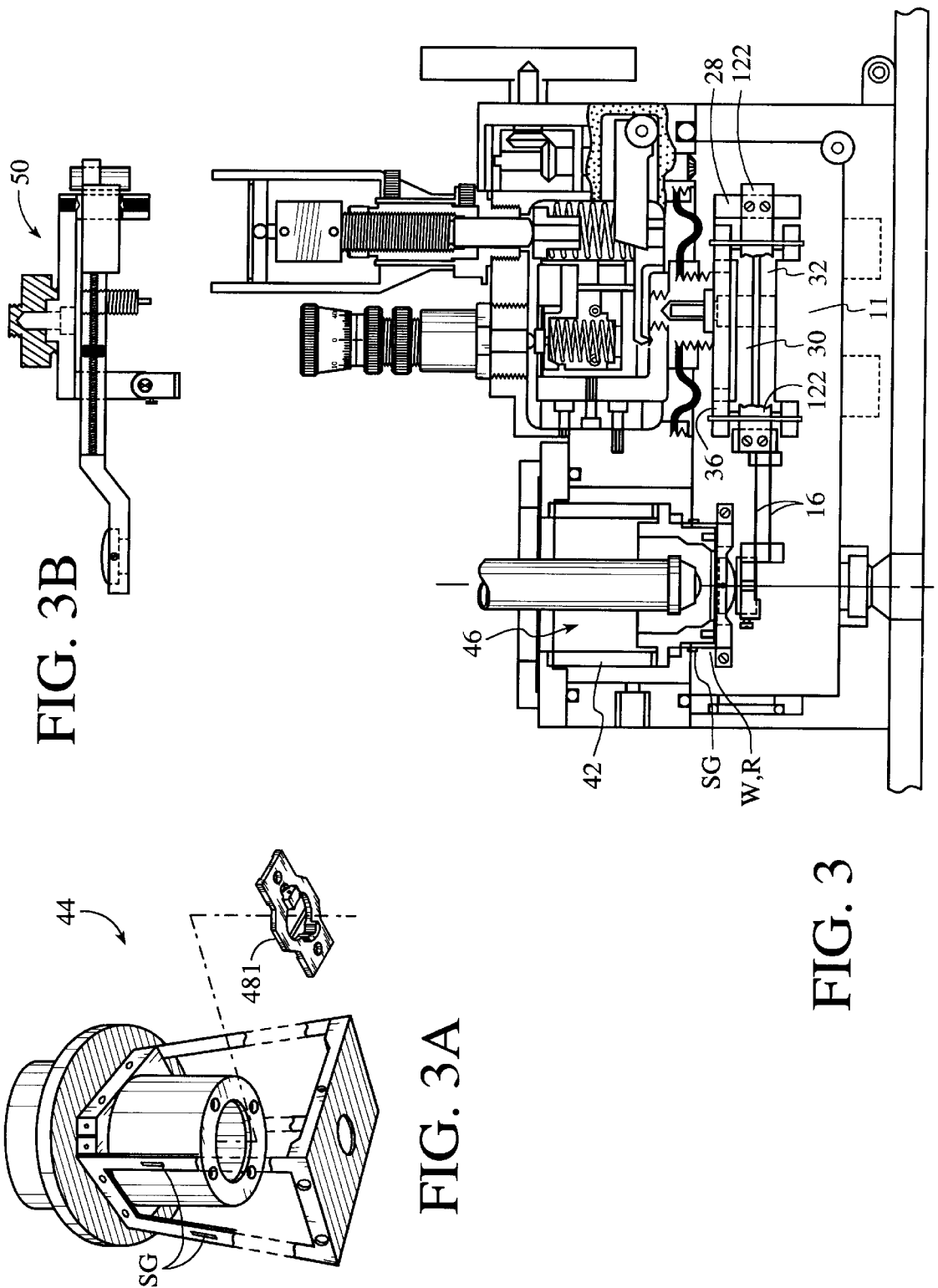
FIG. 3 shows the present invention as assembled for 3D force measurements.

The present invention is a surface forces measuring apparatus (SFA) including miniature rheometers and friction measuring devices. FIG. 3 shows the present invention as assembled for 3D force measurements.

Figure 4:
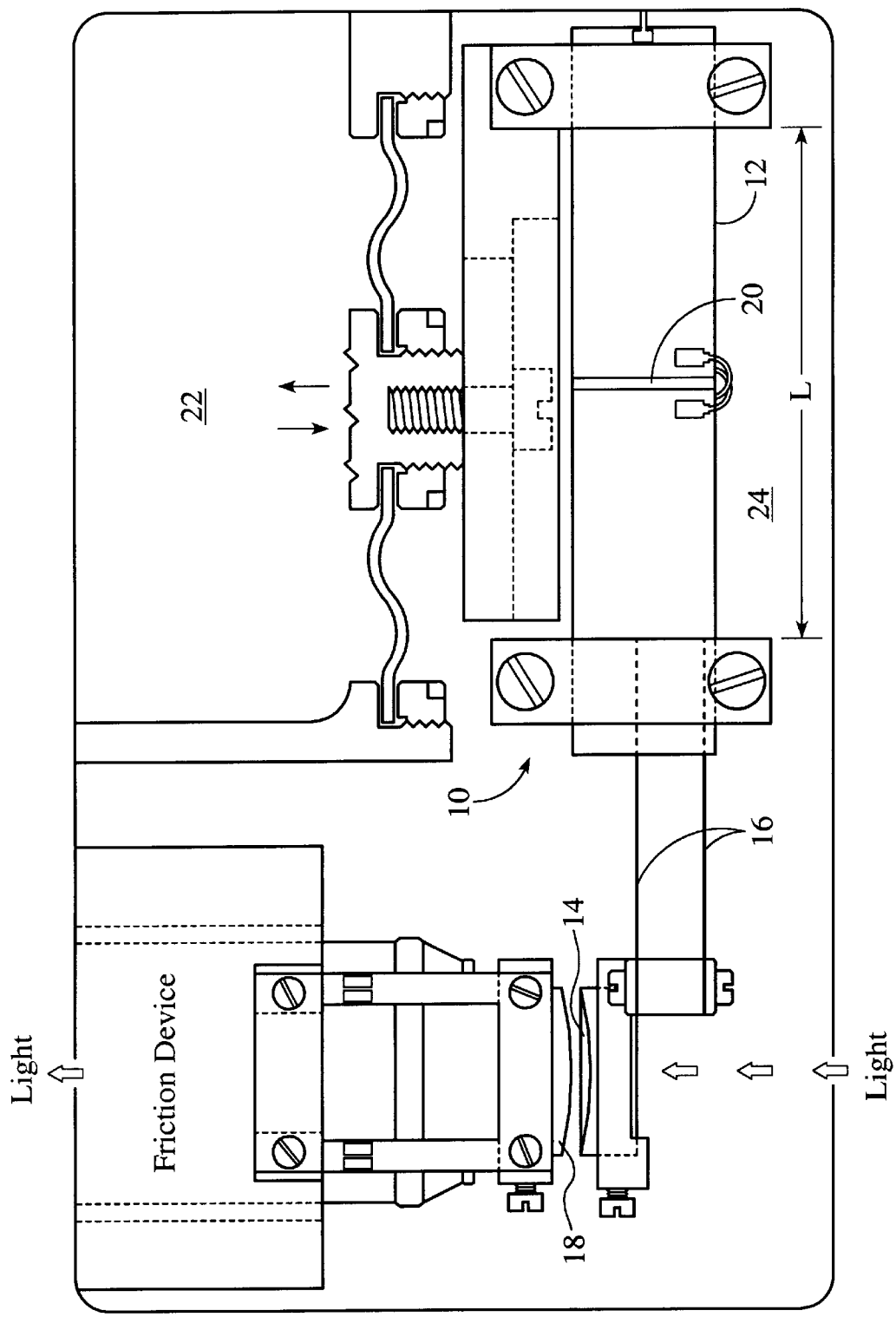
FIG. 4 is a side view of the 2D bimorph slider installed in the SFA.
Figure 5:
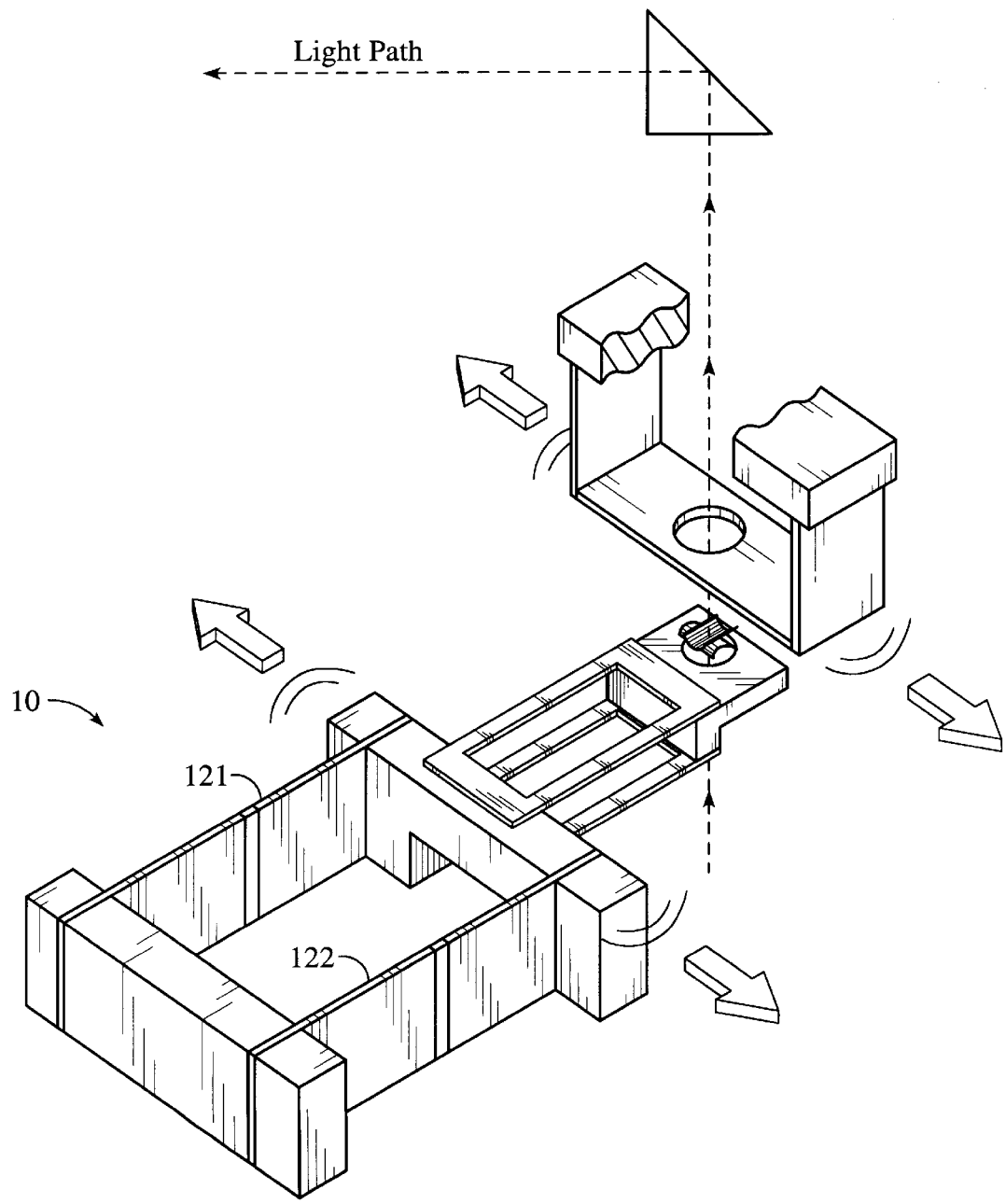
FIG. 5 is a schematic isometric view of the 2D bimorph slider.
Figure 7:
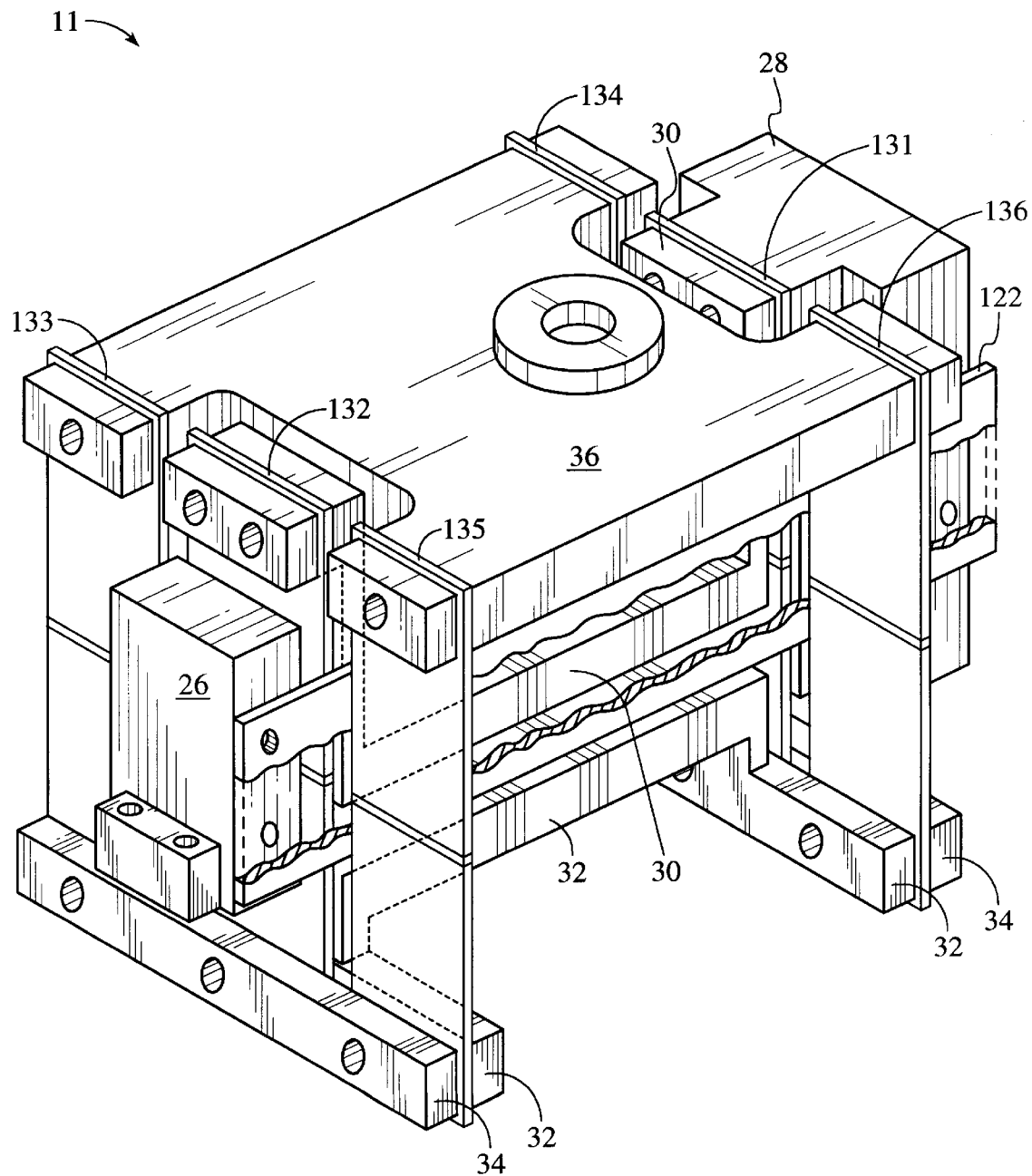
FIG. 7 shows an isometric view of the 3D bimorph slider.

2D Bimorph slider: The 2D bimorph 10 and 3D bimorph 11 sliding attachments (as shown in FIGS. 5 and 7) are displacement transducers allowing for steady, sinusoidal or saw-tooth motion of the lower surface over a range of distances (up to 1 mm) and frequencies (from $10^{-6}$ Hz to >200 kHz). FIG. 4 is a side-view of the 2D bimorph slider which will be described first because it is simpler than the 3D bimorph slider.

Figure 1:
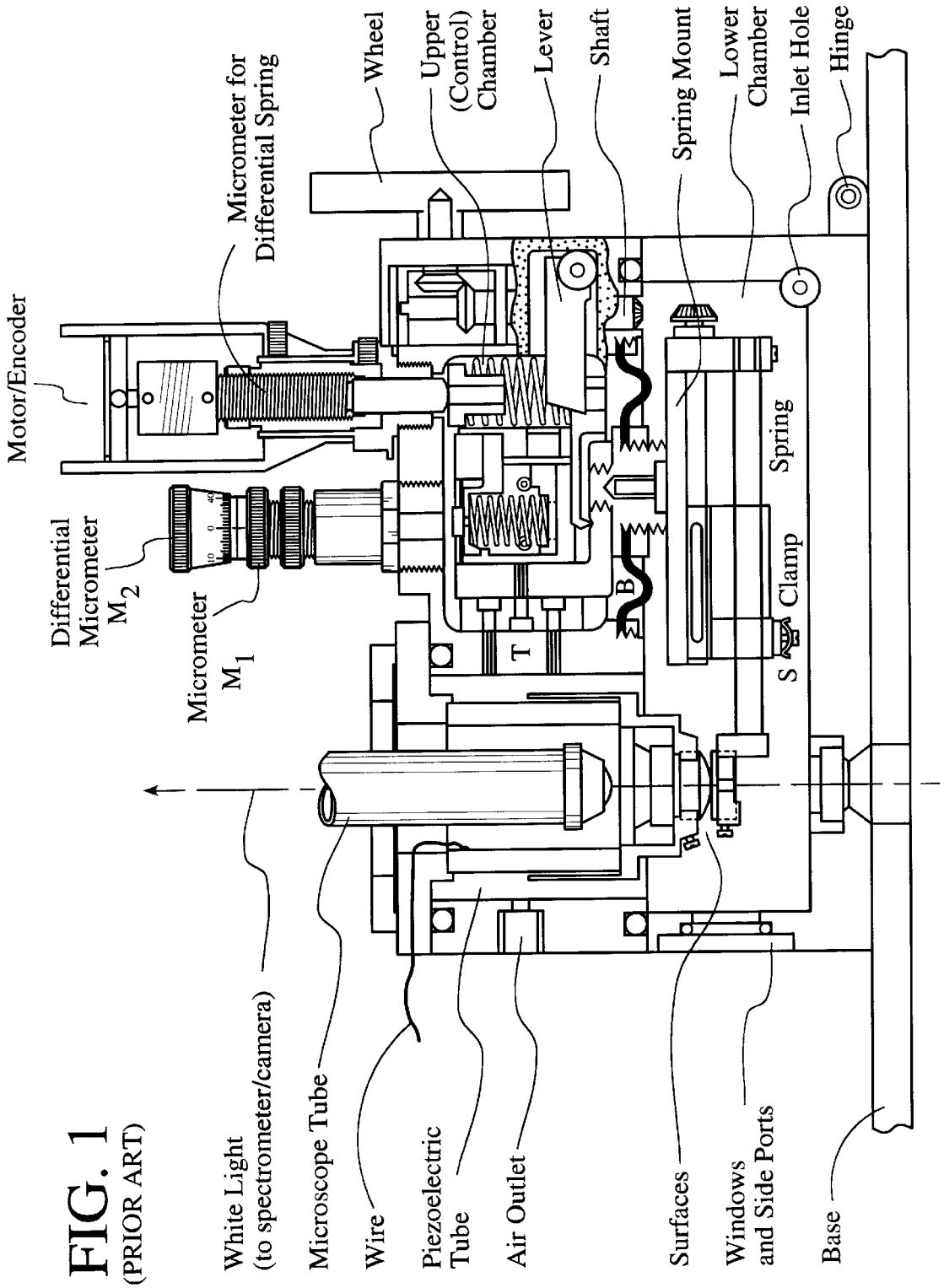
FIG. 1 is a prior art SFA device.

In the present invention, the bimorph slider assembly attachment is interchangeable at B with a variable-stiffness spring (a prior art device as shown in FIG. 1). The bimorphs 12 support the subject lower surface 14 via two cantilever springs 16 (the normal force-measuring springs). The subject upper surface 18 is shown here suspended from the two vertical friction-measuring springs of the 2D Friction Device. Two of the four semi-conductor strain gauges are indicated by SG.

The lower surface 14 is supported at the end of a double-cantilever spring 16 used for measuring the normal forces between the surfaces, as is standard. Lateral movement is accomplished with two (or, for increased driver stiffness, four) parallel piezoelectric bimorph strips 121, 122. The bimorphs 121, 122 are 1 cm wide, 0.021" thick and of active length L which can be varied (see below). Piezoelectric bimorphs are commercially available 'piezoelectric couples' made of two thin sheets of piezoelectric ceramic bonded together by a thin layer of hard conducting material. The two outer faces of each bimorph are coated with thin conducting layers of metal (usually of silver or nickel), which provide protection and serve as suitable electrode surfaces for electrical connections, such as the soldering of connecting wires. Before two piezoelectric sheets are bonded to form a bimorph, their polarity is reversed relative to each other, so that when a DC voltage is applied across the bimorph, one sheet expands lengthwise as the other contracts, resulting in a net bending of the bimorph. For low applied voltages (<100V) the bending, or lateral displacement of each end, is simply proportional to V. Bimorphs are capable of producing much larger displacements than piezoelectric crystals for the same applied voltage. Bimorphs also work in reverse, as force sensors. Thus, when a force is applied to one end a large voltage develops across the two outer electrode faces, which can be easily measured. Suitable bimorphs for use in the present invention are 1 cm wide, 0.021" thick, 2" total length, type PZT 4, nickel coated, from Morgan Matroc Corp.

To convert the pure bending motion of a bimorph into a linear displacement, one may create a 'sectored' bimorph by scraping away a thin strip 20 of the conducting metal coat from the center of each face and then electrically connecting the two pairs of diagonally opposite faces as shown in FIG. 4. This splits the sign of the applied voltage across the two halves (sectors) of the bimorph 12, making each half bend in the opposite direction. If the two halves are of equal length, the resulting effect is a pure linear displacement of the two ends relative to each other, just as occurs with a double-cantilever spring, with no net rotation or bending component. By using two or more parallel bimorphs in this way, a highly robust linear displacement transducer is produced, and this mechanism can be used to drive the lower surface, as shown in FIG. 5.

Referring to FIG. 4, the active length, L, of the sectored bimorph can be adjusted by moving the two clamps, C1 and C2, closer or farther apart. This changes the stiffness of the bimorphs (in proportion to $1/L^3$). An increased stiffness also results in an increased natural frequency of the 'drive' (proportional to $1/L^{3/2}$); however, it is at the expense of a decreasing range of travel for a given applied voltage. Since the two clamps have to be spaced symmetrically about the central strip 20, changing the clamping positions also changes the horizontal position of the lower surface 14. To keep the horizontal distance between the lower surface 14 and connection screw B constant, the whole bimorph slider assembly 10 may be relocated by shifting it to the left or right and then rebolting it to the Upper Chamber 22 with screw B, which is slidably mounted in the slider assembly 10.

The bimorph slider attachment 10 can be used as a normal force-measuring spring via springs 16 and/or as a lateral displacement transducer suitable for shear and friction-type experiments. Normal (i.e., vertical) motion of the slider assembly is effected by a three-stage mechanical translation mechanism involving micrometers and springs, located in the Upper Chamber 22, which has been described in the prior art. Lateral motion is provided by applying a DC or AC voltage to the bimorphs through a coaxial cable connected to the outside of the Lower Chamber 24 via a Teflon-sealed Lemo-type connector.

In some cases, it is desirable to have a 'drive' that can move over a large distance, is very rigid (stiff), and has a high natural frequency. For an active bimorph length of L=35 mm, the range of travel (at 100V across the bimorph) is about ±50 μm, the stiffness of a two-bimorph slider is K≈104 N/m, and the resonant frequency of the drive is approximately 200 Hz. A higher stiffness and resonant frequency can be attained by reducing the active bimorph length, but this generally lowers the travel distance for a given (maximum) voltage. Thus, some compromise is always required, but the ability to readily change the active bimorph length L and the stiffness of the friction force-measuring spring (described below) provides sufficient flexibility for optimizing the system parameters for different types of experiments.

Figure 6:
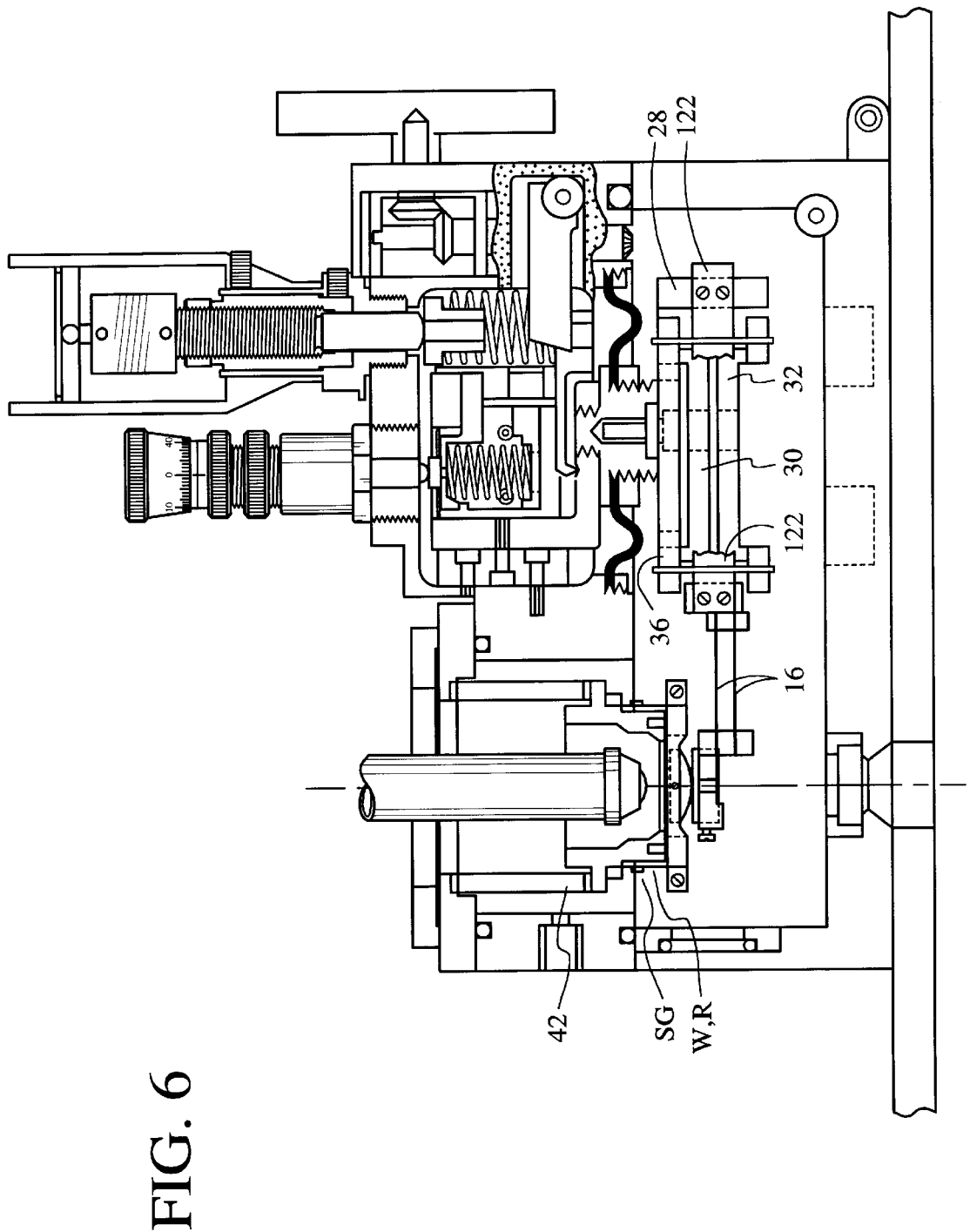
FIG. 6 shows a side-view of the 3D bimorph slider.
Figure 8:
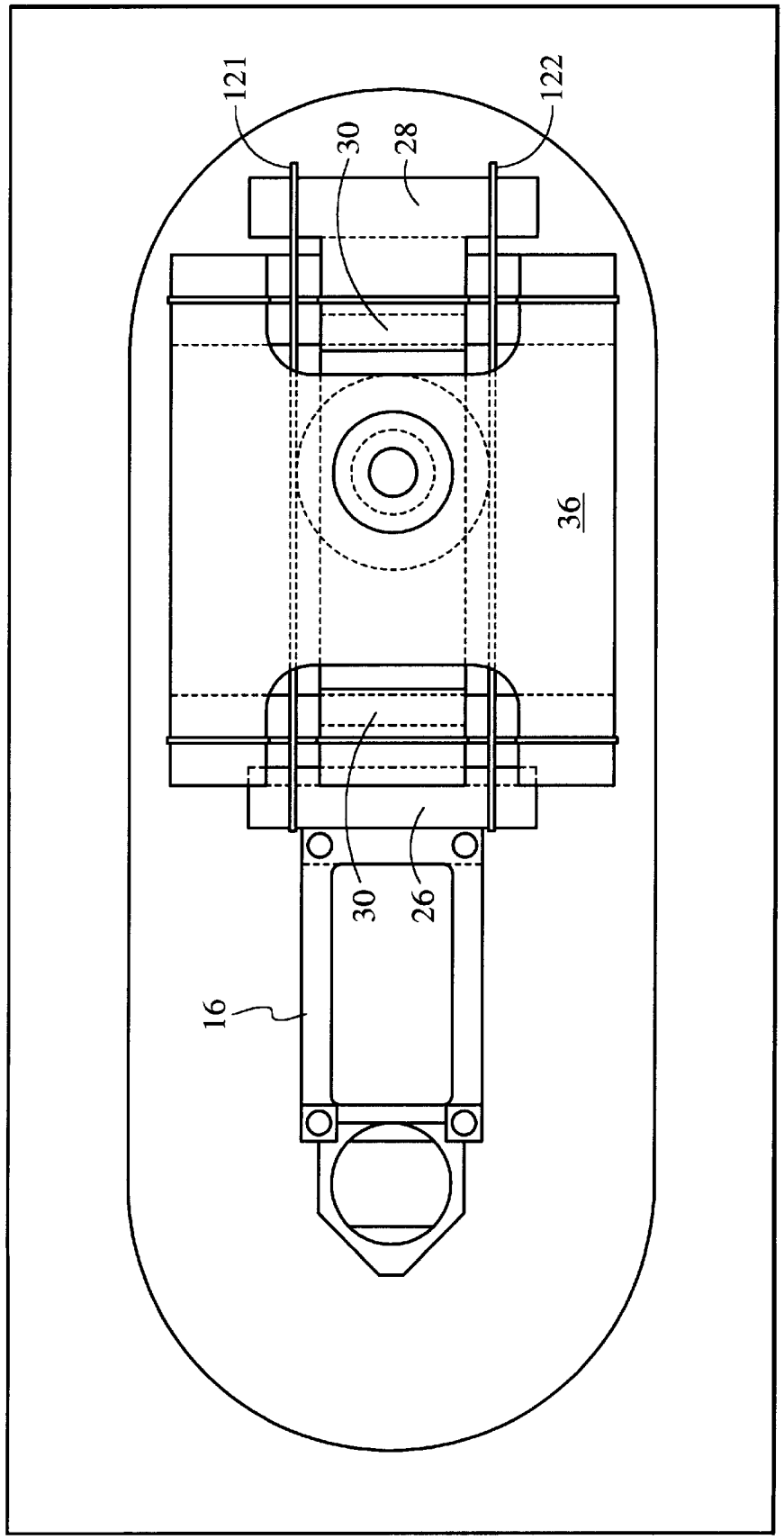
FIG. 8 is a top view of the 3D bimorph detector shown in position inside the Lower Chamber of the present invention.

3D bimorph slider: Referring now to FIGS. 6, 7, and 8, the 3D bimorph slider is interchangeable with the 2D bimorph slider via bolt B. The 3D slider produces motion in the x, y and z directions of the lower surface A via a system of vertical and horizontal sectored piezoelectric bimorphs arranged in orthogonal double-cantilever configurations. The two horizontal force-measuring springs 16 supporting the lower surface 14 are attached to the bimorph slider at block 26, and serve the same function as before, namely, as the means for measuring the normal forces between the surfaces (in the z-direction).

Two identical sectored bimorphs 121, 122, arranged in a horizontal double-cantilever configuration, are attached to block 26 at one end and to the L-shaped block 28 at the other. Block 28 is bolted to the U-shaped brace 30 which is itself held by the two vertical sectored bimorphs 131, 132 clamped to it at their upper ends. At their lower ends, bimorphs 131, 132 are connected to the inverted U-shaped base 32 via base clamps 34. The base 32 and the clamps 34 are then connected to a slider frame 36 via the four sectored bimorphs 133–136. Frame 36 is bolted to the Upper Chamber 22 control unit via bolt B.

The elements that secure the bimorphs are made of 316 stainless steel or of anodized aluminum, and all clamping fixtures to bimorphs are via insulating spacers of mica so that the conducting nickel surfaces of the bimorphs do not make electrical contact with any of the metal surfaces. Electrical contacts with the bimorphs are made by soldering coaxial cables to their conducting surfaces.

Figure 8A:
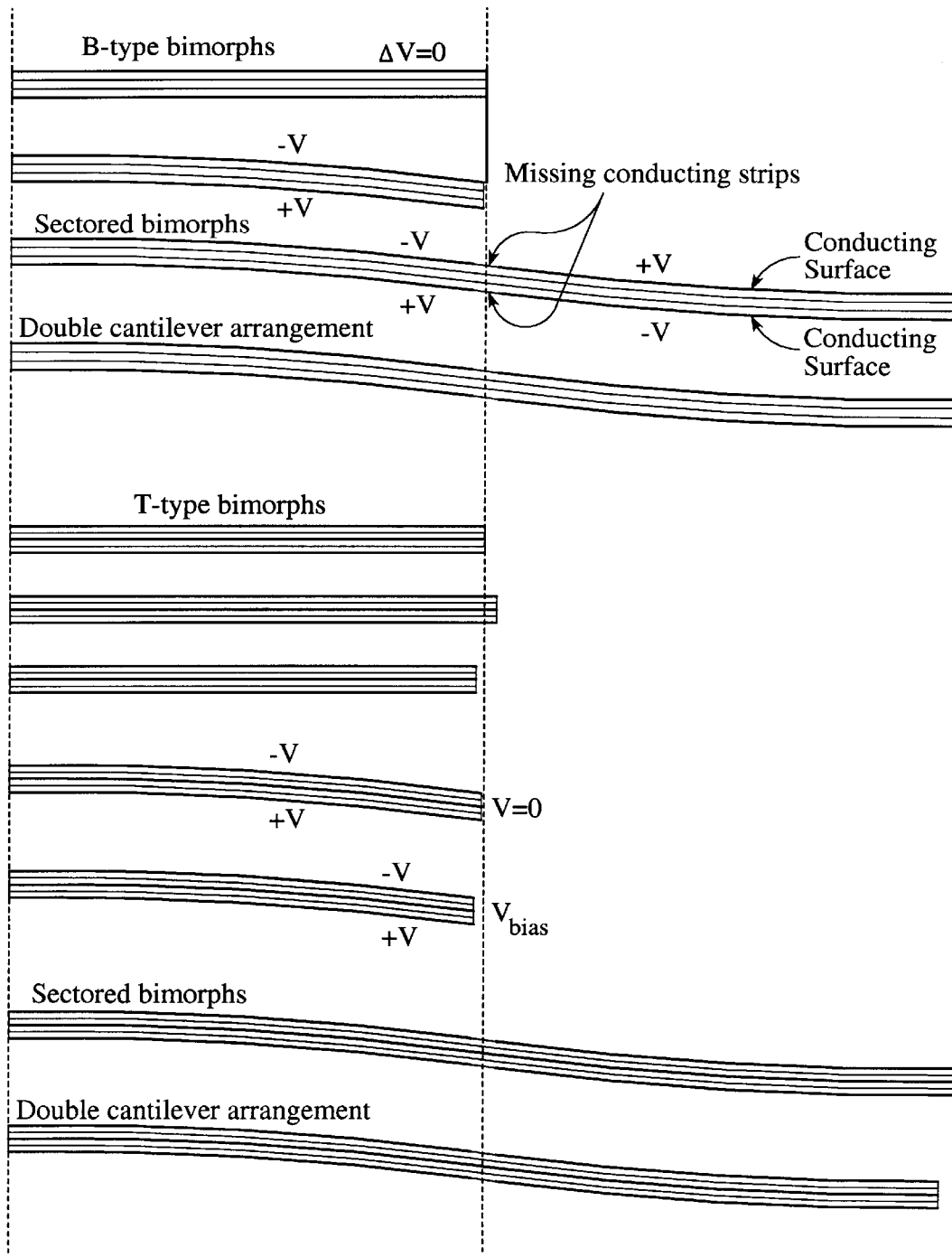
FIG. 8A shows the reaction of T-type bimorphs when different voltages are applied across the inner and outer electrodes.

The vertical bimorphs of the 3D slider are slightly different from those of the 2D slider. They also have a conducting sheet in the middle of the sandwich. These will be referred to as T-type rather than the more common B-type bimorphs. As shown in FIG. 8A, by applying different voltages across the inner and outer electrodes, T-type bimorphs can bend as well as change their length (expand or contract). As will be described later, use is made of this during the operation of the 3D bimorph slider to provide movement in three-dimensions.

FIG. 8A is a comparison of the bimorph configurations used in the 2D and 3D sliders. B-type bimorphs bend when a voltage V is applied across their two outer faces. By reversing the polarity over the two halves of a B-type bimorph, each half bends in the opposite direction. This produces a pure displacement at the other end (with no rotation), rather than a displacement with rotation. T-type bimorphs also have a conducting sheet running through their middle. By applying appropriate voltages across the three conducting surfaces, such bimorphs can be made to bend in either direction as well as stretch or contract at the same time.

Friction Devices (2D and 3D detectors) and Fixed Upper Support: FIGS. 9–13 show various embodiments of the Piezo Mount which can support three interchangeable units: the Fixed Support, the 2D and 3D force-detecting attachments (Friction Devices) which are used to measure the lateral (frictional) forces produced on the upper surface due to the motion of the lower surface. Each of these three attachments is designed to carry a silica disk for supporting the upper surface.

Figure 9:
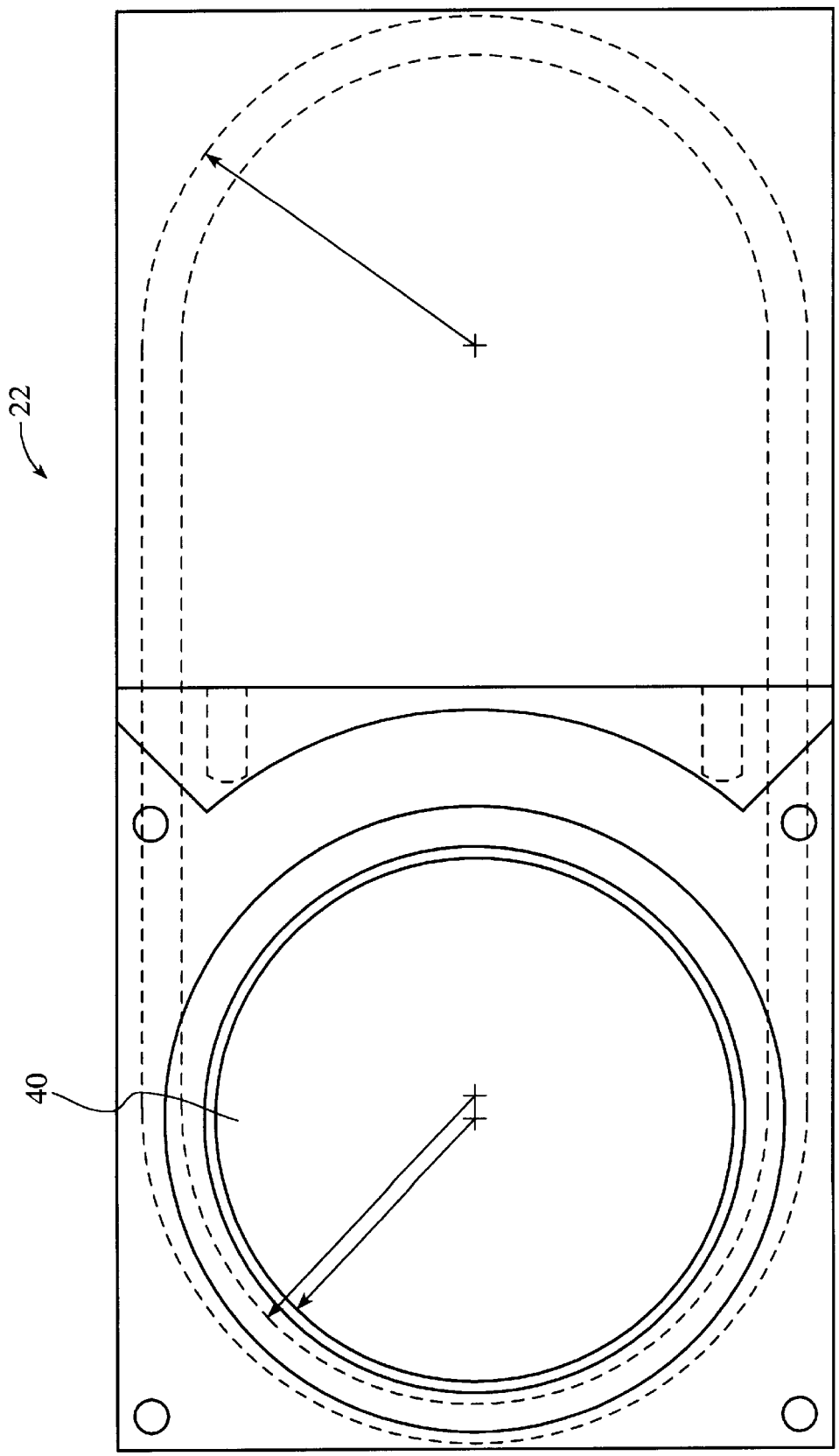
FIG. 9 is a top view of the upper chamber.

FIG. 9 shows a round hole 40 in the Upper Chamber 22 of the present invention for positioning the Piezo Mount 42. The Piezo Mount 42, shown in FIGS. 10 and 11, serves as the means for attaching the 2D detector 44 and the 3D detector 46 (Friction Devices), shown in FIGS. 13 and 12 respectively, and the Fixed Support 481 for the upper surface 18, shown in FIG. 13. These three attachments can be used interchangeably, and will now be described in turn.

Figure 10:
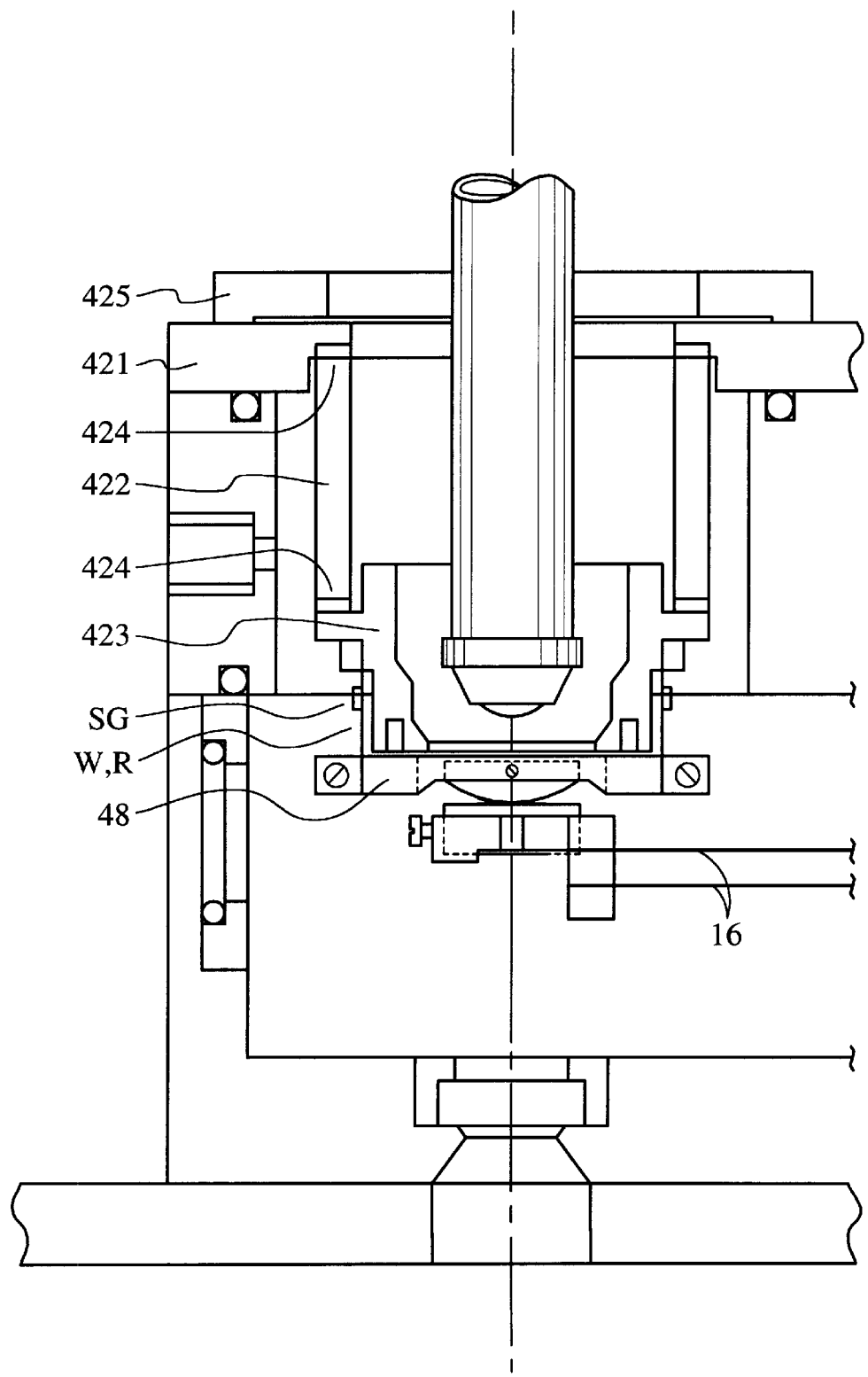
FIG. 10 shows the Piezo Mount fitted into the Upper Chamber.
Figure 12:
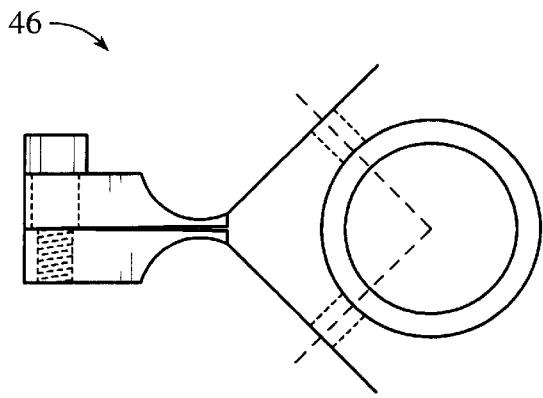
FIG. 12 illustrates a detailed portion of the 3D detector (Friction Device).
Figure 13A:
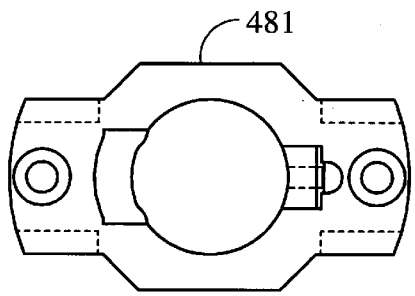
FIGS. 13A–E illustrates the 2D detector (Friction Device).
Figure 13B:
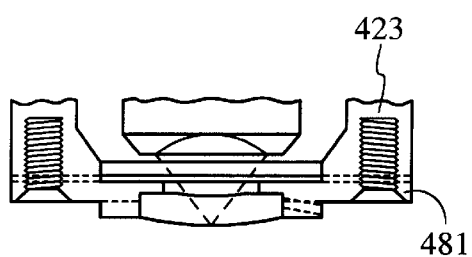
Figure 13C:
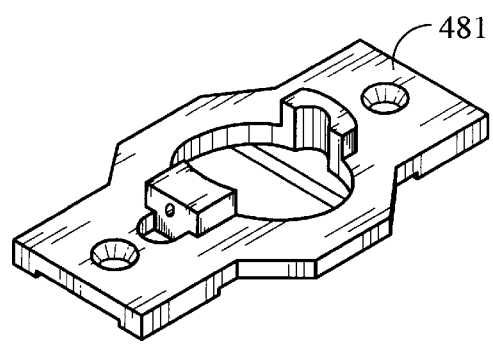
Figure 13D:
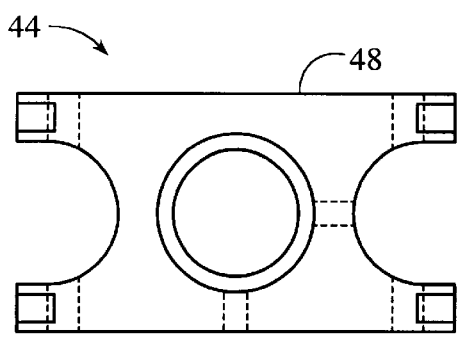
Figure 13E:
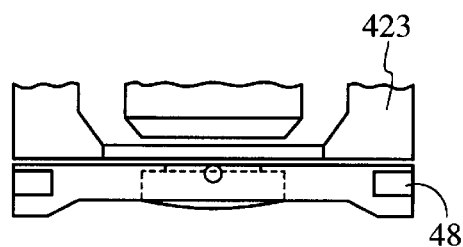

Piezo Mount: Referring to FIGS. 10 and 11, the piezo mount 42 consists of the top 421 to which is glued the piezoelectric crystal tube 422. The other end of the piezo tube 422 is glued to the mount 423. A non-conducting epoxy glue is used for this gluing, and thin insulating spacers 424 (0.01" thick) are further used to electrically separate the piezo tube 422 from its mountings. The piezo mount 42 fits into the upper chamber 22 as shown in FIG. 10, and is clamped securely into position by the clamp 425.

3D Friction Device: The 3D Detector (see FIGS. 10 and 12) is connected to mount 423 of the piezo mount 42 via four parallel spring wires of equal dimensions that pass through matching holes in the mount 423 and an upper surface frame 48. The wires are clamped in place by four screws on frame 48 and are clamped to the mount 423. The 4-wire arrangement resembles a square table that is held upside-down from its four thin-round legs. Note that with this arrangement, the 'table' can be moved independently in the x and y directions, as well as rotated about the vertical z-axis. Semi-conductor strain gauges SG are attached to the wires (legs) at different places so that bending of the wires in different directions can be recorded with a multi-channel strain gauge bridge. This attachment can therefore be used to measure lateral displacements and friction forces acting on the upper surface simultaneously in the x and y directions (this is in addition to measuring normal forces in the z-direction using the piezo tube 422 and springs 16 as described in the prior art).

2D Friction Device: The 2D Detector is shown in FIGS. 3 and 13A–E. Frame 48 is attached to two vertical double-cantilever springs which are clamped at their other ends to mount 423. Resistance or semi-conductor strain-gauges (SG) are attached to these springs as shown (FIG. 3). This attachment can be used to measure lateral displacements and friction forces acting on the upper surface in the x or y directions (this is in addition to measuring normal forces in the z-direction using the piezo tube 422 and springs 16 as described in the prior art).

Fixed Upper Support: FIG. 13 also shows the fixed support 481 for the upper silica disk holding the upper surfaces. This part can be bolted to mount 423 of the piezo mount 42 as shown in FIG. 3, and used as in the prior art (cf. FIG. 1).

Figure 2:
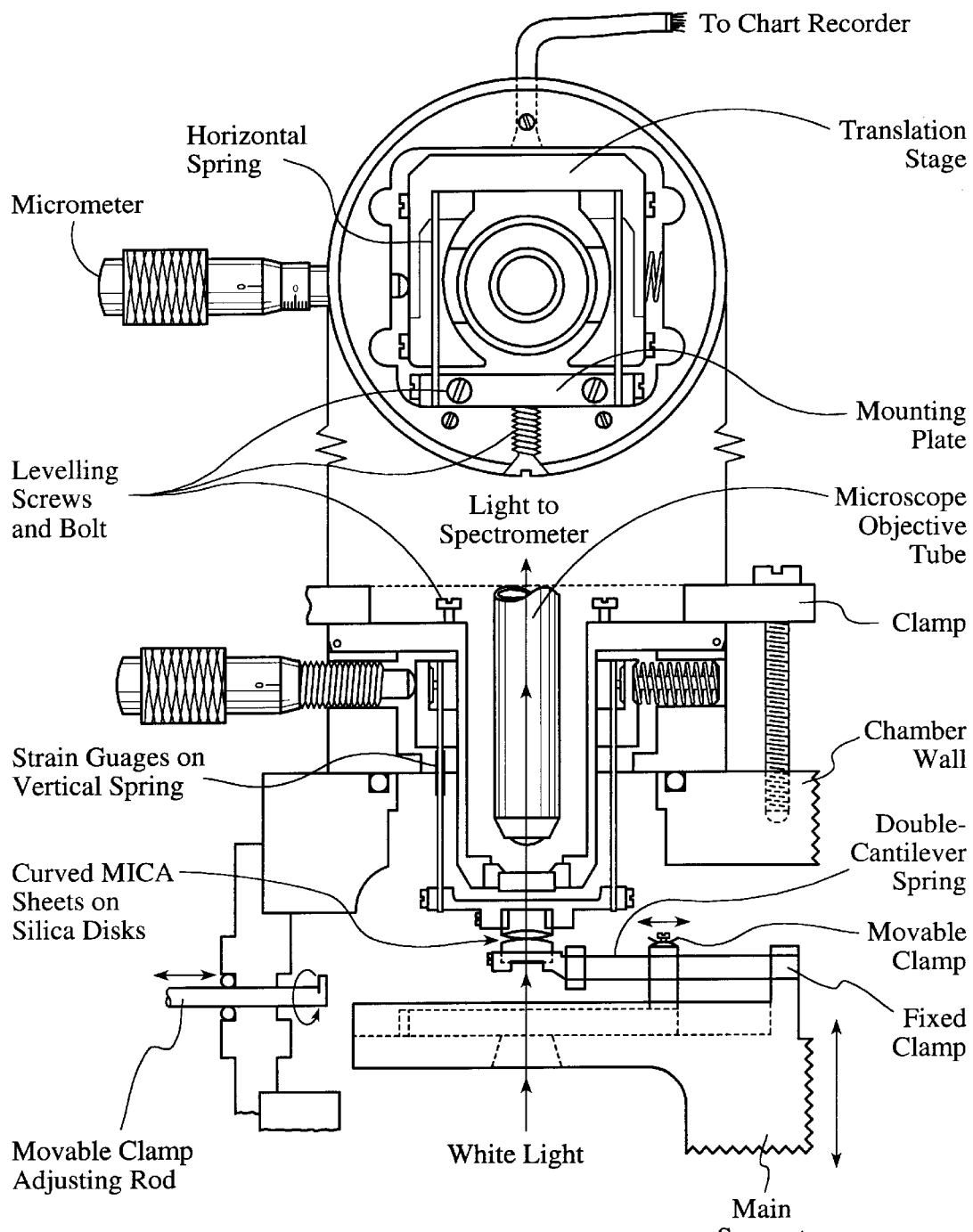
FIG. 2 is a depiction showing a prior art Friction Attachment.

Mechanical Friction Device (Attachment): FIG. 2 shows the original Friction Attachment used in the SFA Mk 2. A similar attachment has been designed for use with the present invention. A side view of this is shown in FIG. 4. This friction attachment has the capability of driving the upper surface at a constant speed using a mechanical drive that is powered by a variable speed DC motor with an encoder readout. The total distance of travel is much larger than can be attained with bimorphs: ~5 mm instead of ~1 mm. However, only a limited range of velocities are practical, these being dictated by mechanical noise (vibrations) at both high and low speeds. In addition, sinusoidal and other types of motions cannot be easily generated with motors, and the Mechanical device lacks the piezoelectric fine distance control. Nevertheless, the Mechanical Friction Attachment is a complete, self-contained unit, capable of both generating movement and measuring the resulting friction forces via strain gauges (SG in FIG. 4), while the Piezo Mount cannot be used to measure lateral forces independently without the Bimorph Slider.

Figure 14A:
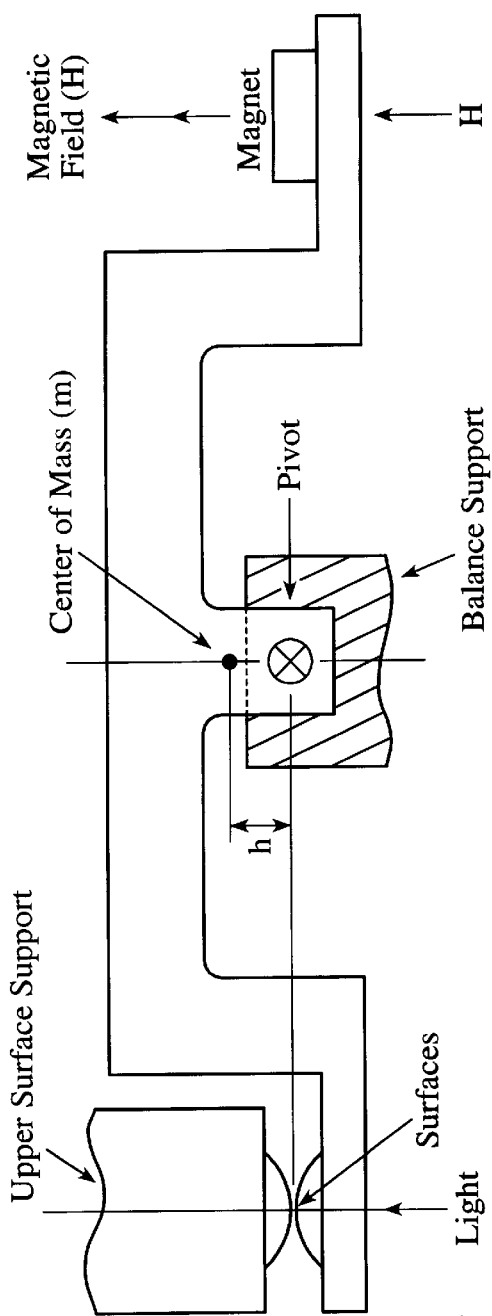
FIG. 14A is a schematic view of the Balance assembly.
Figure 14B:
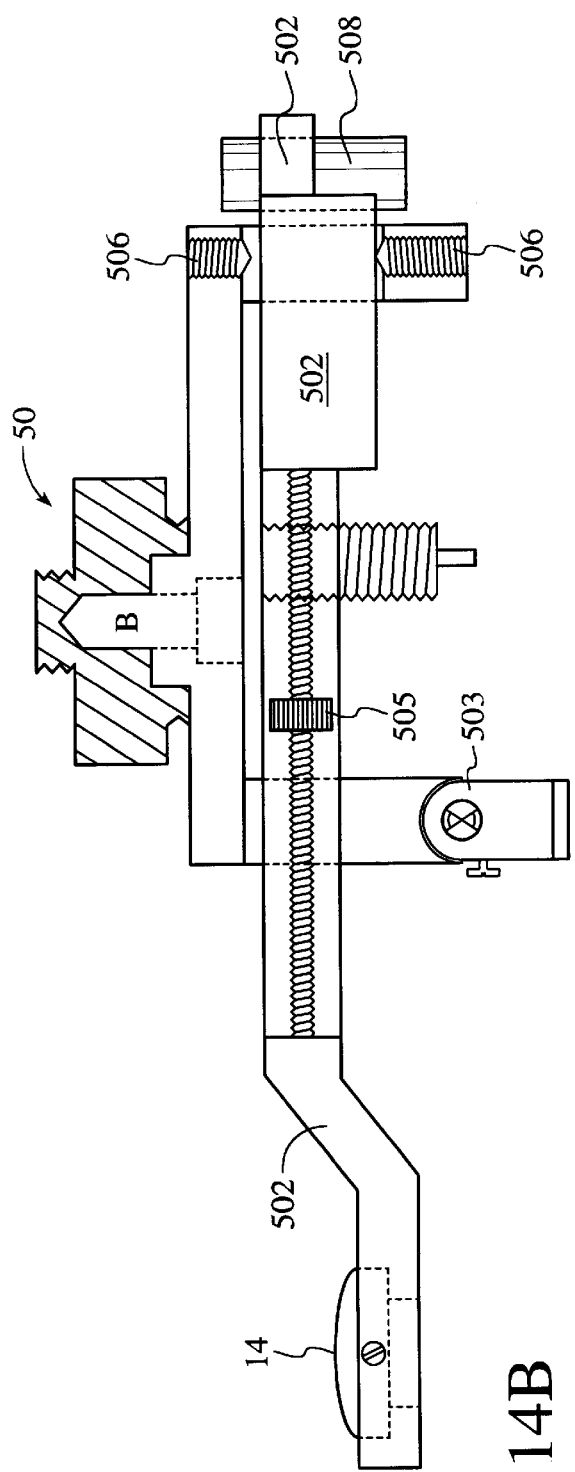
FIG. 14B is a cross section of the Balance assembly of the present invention.

Balance Attachment: This attachment, shown in FIGS. 3B and 14A–B, is used to measure forces that take a long time to reach equilibrium as well as very weak forces. To measure such forces, one must either totally prevent thermal drifts, which is practically impossible, or one may devise a method that can still reliably measure surface forces even in the presence of such drifts. This is the purpose of the balance attachment 50. The balance attachment 50 is used to measure only the normal forces between two surfaces. To do this, the piezo mount 42 should carry the fixed support 481.

The balance assembly 50 can be bolted to the upper chamber 22 with screw B through the carrier 501. Referring to FIG. 14B, the balance arm 502 is held by a cross-spring flexure pivot 503 which ensures frictionless rotation about a horizontal axis passing through the pivot point. Screws 504 and 505 on the arm 502 can be adjusted to ensure zero or near zero restoring force on the balance, and screws 506 and 507 on the Carrier 501 act as end-stops. A permanent, low hysteresis magnet 508 is attached to one end of the balance arm 502, and the lower surface 14 is secured at the other end of the balance arm 502. By applying a uniform vertical magnetic field from outside the apparatus, a constant vertical force acts on the magnet, which does not change even if the pivot drifts away from its original position either in the x, y or z directions (the latter because the balance has zero or near-zero restoring force, as described below). Thus, equilibrium inter-surface forces can be measured with the Balance Attachment regardless of how long it takes the forces to equilibrate.

Principles of the 'constant force' Balance Attachment: The Balance Attachment is a totally new method for measuring forces, and so it will now be described in full detail.

There are a number of methods for directly measuring the forces between two surfaces or particles. By far the most common is the 'spring-deflection method' whereby one of the surfaces is supported at the end of a 'force-measuring' spring whose deflection is measured as the two surfaces are made to approach each other. This method is behind the surface forces apparatus (SFA), the atomic force microscope (AFM), and a number of other force-measuring techniques developed for particular systems.

One problem with all force-measuring techniques that rely on the restoring force of a spring is that they cannot compensate for any possible thermal drifts between the coordinate system located at the mid-point between the two surfaces and the location of the base of the force-measuring spring. When the time to reach equilibrium is rapid compared to thermal drift over that time (and the natural decay time of the spring), the problem is unimportant. But in practice, for times longer than a few minutes, it becomes increasingly more serious since thermal drifts of the order of angstroms may now occur and these will show up as an apparent force between the two surfaces. For even longer equilibration times, e.g., of the order of hours or days, these methods become completely unreliable for measuring sensitive forces, and there have been many cases where the true equilibrium interaction cannot be measured or where erroneous data was recorded due to drifts or insufficient equilibration times.

These deficiencies become particularly important for surfaces interacting across polymer fluids or when the surfaces have polymer or surfactant layers adsorbed on them. In such cases equilibration times of the order of days or even months have been reported. Unexpectedly long equilibration times have also been reported for simple liquids confined between two solid surfaces where the relaxation times of the 'trapped' liquid molecules may be as much as 10 orders of magnitude longer than in the bulk liquids.

It is not possible to completely avoid thermal drifts, and even if one could do this, for example, by performing pre- and post-experiment calibrations, one could not be certain what the drift was during the actual experiment. Thus, over a sufficiently long time period, any thermal drift of the spring clamping position will be recorded (measured) and interpreted as a changing force between the surfaces.

One way to reduce this problem is to have good thermostating. The other is to employ weak force-measuring springs. Thus, if K is the spring stiffness and if over a given time period the base of the spring drifts by a distance $\Delta D$, the uncertainty in any subsequent force measurement will be $K\Delta D$. For typical low values of K=1–100 N/m, and assuming a drift of $\Delta D$=0.1–100 nm, the error in measuring forces will therefore be $10^{-10}$–$10^{-5}$N. While the lower limit may be acceptable for many cases, the upper limit certainly is not. One may, of course, construct extremely weak force-measuring springs. This will not only reduce the measuring errors, but also increase the sensitivity of the force measurements themselves. However, this works only in theory. In practice, other factors must also be considered when designing a force-measuring spring, and these are not so advantageous. First, weaker springs take longer to reach equilibrium. Second, these springs usually have to support one of the surfaces; if they are very weak they will sag a long way under the weight of the surface, perhaps beyond their elastic limit. Third, the supported surface will become very susceptible to picking up vibrations. Four, these springs usually function as linear displacement guides, for example, they must be designed to allow for vertical displacement of the surface (in the z-direction), but not in the x- or y-directions, and they should not be able to rotate (twist or bend) about any axis. These design requirements are increasingly difficult to meet the weaker the springs become. Thus, even though a weaker spring may be effective in reducing the measuring error, there are limits beyond which it cannot eliminate the practical problem.

The root of the problem with using springs is that the restoring force of a spring depends on how much it is deflected, so that if one wants to apply a constant force for a long time, one must ensure that this deflection remains constant over that time. One way of avoiding the problem is to eliminate the use of force-measuring spring altogether, and instead to apply a constant force by some other means. FIG. 14A shows a schematic drawing of a 'constant-force balance' that in principle meets all the operational requirements of a constant-force transducer, including robustness in all other directions, that is also insensitive to thermal drifts.

The principle of this balance as follows. Imagine that the balance arm is pivoted by a frictionless knife-edge pivot, and that the center of mass of the whole balance is also located at the pivot. The balance will then have no restoring force when displaced, and in principle it should remain at whatever angle it is left at. If the left arm supports one of the two surfaces and the right arm has a magnet attached to it, then by applying a magnetic field on the magnet a force will be felt on the other side, trying to displace the surface up or down. If, over the distance $\Delta D$ the magnetic field remains uniform, then it is clear that any thermal drifts of the pivoting point relative to the upper or lower surfaces will have no effect on the applied force on the lower surface. For example, if under a given field the lower surface experiences an upward force F which brings it to an equilibrium separation of D=100 Å from the upper surface (where F is exactly balanced by a repulsive intermolecular force acting between the two surfaces), and if after 10 hours the pivot has drifted upwards by 150 Å, the two surfaces will still be at D=100 Å from each other (so long as the magnetic field is uniform over these small distances).

Design of constant-force balance: In practice, it is not possible to construct a frictionless knife-edge pivot. The closest one can approach a totally frictionless pivot is to use a combination of metal leaf springs that provide frictionless rotation about some axis. The 'cross-spring flexure pivot' is one such design. This type of miniature pivot was successfully used in some early friction measurements and it is also used in the present force balance. Unfortunately, this type of pivot produces a restoring force when it rotates, that is, it has a small but finite elastic stiffness or torque. However, designing the balance so that the center of mass is located above the pivot (see FIG. 14A) introduces a new (opposing) torque into the rotation due to gravitational or buoyancy forces. This opposing torque can be made to offset exactly the torque of the flexure pivot.

Put in mathematical terms, referring to FIG. 14A, if m is the weight of the balance whose center of mass is at a distance h above the pivot point, then when the balance rotates through an angle $\theta$ there will be a 'gravitational' torque of magnitude $mgh\sin\theta \approx mgh\theta$ acting to rotate the balance further. On the other hand, the flexure pivot itself will have developed a restoring torque of magnitude $\tau\theta$, acting in opposition the gravitational torque. Thus, if $mgh=\tau$ the two effects cancel out, and the balance will behave as a frictionless zero-stiffness balance. This condition can be expressed as $h=\tau/mg$.

FIG. 14B shows a detailed drawing of the constant-force balance that can be used with the SFA of the present invention. The balance is made of aluminum (anodized) and weighs about m=20 gm. The pivot is a commercial flexure pivot (Bendix Corp.) of torque constant $\tau=10^{-4}$N m deg$^{-1}$, and is mounted at a height $h=\tau/mg=5$ mm below the center of mass of the balance. Small horizontal and vertical adjusting screws 504 and 505 are used to finally obtain an overall restoring torque of zero (screw 504 can be adjusted from outside the apparatus via an adjustable forked shaft that passes through the floor of the apparatus and that can be maneuvered from the outside).

With this arrangement, by applying a uniform vertical magnetic field across the permanent magnet 508, a constant, time-independent force is produced on the lower the surface. Additional features of the balance include two end-stop screws 506 and 507 to prevent accidental large deflections, and the ability to relocate the position of the surface A within the chamber over a distance of ±5 mm in the x and y directions.

OPERATION OF THE INVENTION

General operating procedures Optical operations: Surface shapes and separations are measured, as in prior SFA's, using the FECO-fringe optical technique which involves interfacing the instrument with a normal light microscope that in turn directs the emerging light onto a grating spectrometer. The enlarged objective-lens opening of the new instrument and the shorter path length from the surfaces to the microscope objective now allows for a greater variety of optical techniques, such as more high powered objectives and fluorescence microscopes, to be interfaced with the new instrument.

Vertical displacement of the surfaces: Surfaces are moved towards or away from each other (in the z-direction) by simultaneously activating one or more of the following displacement mechanisms: The three Upper Chamber micrometers (see FIGS. 1 and 3), which can be operated either by hand (manually) or via reversible DC motors with encoder read-outs. The piezoelectric crystal tubes are operated by applying a voltage across their inner and outer walls which causes them to expand or contract by 5–10 Å per volt, depending on the wall thickness (typically ⅛ in) and tube length (typically 1 in).

Measurement of normal forces: Normal forces (in the z-direction) are obtained by measuring the deflection of the double-cantilever force-measuring springs 16 (FIG. 4) using the optical FECO technique as described in the prior art.

Lateral displacement of the surfaces: The 2D and 3D bimorph sliding attachments are displacement transducers that can be driven by a commercial function generator to produce steady, sinusoidal or saw-tooth motion of the lower surface over a range of distances (up to 1 mm) and frequencies (from $10^{-6}$ Hz to >200 kHz). Surfaces are displaced laterally in the x- and y- directions by using various combinations of sectored bimorphs arranged in double-cantilever configurations whose bending and displacements are graphed in FIG. 8A.

The 2D slider (FIGS. 4 and 5) produces linear motion (only) in the x-direction when a voltage is applied across the sectored bimorphs. The displacement is about 50 $\mu$m per 100V, depending on the free length L of the bimorphs.

The 3D slider (FIGS. 6, 7, 8) can be used to generate motion in all three directions by applying different voltages across the 8 sectored bimorphs 121, 122, and 131–136. Referring to FIGS. 7 and 8A, and remembering that slider frame 36 is fixed, being rigidly attached to the apparatus at B, one can see that applying a voltage to bimorphs 121, 122 will cause the block 26 to move linearly in the x-direction (which in turn will displace the surfaces which are suspended from block 26 via springs 16). Likewise, applying a voltage across bimorphs 131, 132 will cause brace 30 and block 28 to displace linearly in the y-direction (with base 32 remaining fixed) thereby displacing the surfaces by the same amount, say D. If one simultaneously applies the same voltage across bimorphs 133/134 and 135/136, but in the opposite direction, this will cause these bimorphs to bend by the same amount but in the opposite y-direction. Since frame 36 is fixed, the overall effect will be a shift in base 32 relative to frame 36 by D, and a shift in brace 30 and block 28 relative to base 32 by D, that is, a total linear shift of the surfaces in the y-direction by 2D. In addition, there will be no vertical displacement of the surfaces since the two small vertical displacements of bimorphs 131 and 132 will cancel out the vertical displacement of bimorphs 133–136. Finally, bimorphs 133–136 are of the T-type rather than the B-type (FIG. 8A). Thus, by applying different bias voltages $V_{bias}$ to the even and odd numbered bimorphs, then in addition to a pure linear displacement in the y-direction, the bimorphs will also expand or shrink along their lengths by a small amount. If different bias voltages are applied across the odd and even numbered bimorphs, the net effect will be a tilting or rotation of brace 30 and block 28 about an axis in the x-direction such that the lower surface 14 is lifted up or depressed in the z-direction. In this way, by applying different voltages and bias voltages across the eight bimorphs, it is possible to generate relative movement of the surfaces 14 and 18 in any desired direction in the x-y-z coordinate system.

In sliding experiments, it is often desirable to have surfaces moving at some constant speed, rather than sinusoidally. This can be achieved with the bimorph slider by applying a triangular voltage signal to the bimorphs. This produces constant velocity motion in one direction, then back gain, repeatedly. In this way, very low and very high constant velocities can be achieved. For example, using the above operating parameters, the range of practical speeds attainable using a function generator that provides signals in the $\mu$Hz to MHz range over a total distance of about 100 $\mu$m is from ~1 Å/s to ~1 m/s—a dynamic range of 10 decades (10 orders of magnitude).

Measurement of lateral forces: Lateral forces of the 2D and 3D Detectors are measured from the resistance changes of the miniature semi-conductor strain gauges SG attached to the friction springs W or wires R (see FIG. 10) (these gauges are about 100 times more sensitive than resistance strain gauges). The 3D Detector wires employ 8 strain gauges in a two bridge configuration from which displacements in the x- and y-directions can be independently measured. The 2D Detector operates in a similar fashion, except that it has only four strain gauges in a single bridge configuration. The rapidly changing friction forces are most suitably recorded on a normal storage scope or data-storage system for later analysis, but more slowly varying forces can be recorded on a paper chart recorder.

The mass M of the upper surface or 'stage' and the dimensions of the friction force-measuring springs (length, width, and thickness) can be easily changed, if necessary, to optimize their performance, depending on the requirements: (i) high force sensitivity (bridge output voltage vs friction force), or (ii) high displacement sensitivity (output voltage vs lateral displacement), or (iii) high natural frequency of the 'stage', thereby increasing its dynamic range and therefore the ability to faithfully measure rapid transient effects such as stick-slip friction. Typical optimum values used are: K=$10^4$ N/m, M=2.2 g, f=330 Hz. When used with a standard commercial strain-gauge amplifier and chart recorder or storage scope recorder, the DC friction force sensitivity is about 50 $\mu$/N, which corresponds to a lateral displacement of 5 nm. Much greater sensitivities can be obtained when used in AC mode with a lock-in amplifier (such as a Stanford Research Systems digital two-phase lock-in amplifier Model SR830) which also allows independent measurements of the in-phase and out of phase components of the output signal.

Operating the Balance Attachment: In many respects, making force measurements with the balance attachment is not very different from making conventional measurements with force-measuring springs. Once mounted into the SFA, surface separations are measured using the same optical technique as before, and the surfaces can be brought towards each other using motors and piezoelectric transducers as before, with added control from the magnetic field which can be adjusted by varying the current across an electromagnet.

In a typical force run, the balance arm is first 'levelled' with the two levelling screws. The two surfaces are then moved in the normal way and brought to within, say, 50 nm of each other, where the inter-surface force is still zero. Now, however, the two surfaces are moved closer together—not mechanically or via the piezo crystal—but by increasing the current through the electromagnet. If there were no force between the surfaces, they would continue to move towards each other until they come into contact. If there is a repulsive force-law, given by F(D), the two surfaces will move until equilibrium is established at a separation D given by F(D) =$K_c$I, where $K_c$ is the (previously calibrated) magnetic force per unit current I. On the other hand, if the force is attractive, the two surfaces will continue to move until they come into contact. On separating the two surfaces from contact they will spontaneously jump apart once $K_c$I reaches the adhesion force. It is also be possible to do time-dependent studies, e.g., measuring drainage times and jump rates, with this type of balance, as well as simulate colloidal collisions.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

I claim:

1. A device for measuring forces between two surfaces comprising:
    a first means for mounting an upper surface, said upper surface mounting means comprises a means to measure movement of said upper surface,
    a second means for mounting a lower surface in proximity to said upper surface, said lower surface mounting means also comprising a movement means to provide adjustable movement of said lower surface along a first axis, along a second axis orthogonal to said first axis, and along a third axis orthogonal to both said first and said second axes, said movement means is capable of providing said adjustable movement along said three axes simultaneously,
    a spring means coupled between said second mounting means and said adjustable movement means, said spring means deflects as a function of said forces between said upper and said lower surfaces, said spring means having a spring force constant;
    a light means to direct a beam of white light along said third axis through said upper and said lower surfaces to provide optical interference fringes when said white light passes through said upper and said lower surfaces, said interference fringes being a first measure of a distance between said upper and said lower surfaces; and wherein
    a distance between said upper and said lower surfaces as adjusted by said first movement means is a second measure of the distance between said upper and said lower surfaces, any difference between said first and second measures being a function of said forces between said upper and said lower surfaces and said spring force constant, said device is capable of measuring said adjustable movement along said three axes simultaneously.

2. The device of claim 1 wherein:
    said movement means comprises a frame having first and second ends,
    a base having first and second ends, said base extending between said first and second ends of said frame, said base is movable between said first and said second ends of said frame,
    a brace having first and second ends, said brace extending between said first and second ends of said frame,
    a plurality of bimorph means,
    means for applying an electrical potential to each of said bimorph means,
    at least a first one of said bimorph means is mounted between a first end of said base and a first end of said frame, at least a second one of said bimorph means is mounted between a second end of said base and a second end of said frame, at least a third one of said bimorph means is mounted between said first end of said base and a first end of said brace, at least a fourth one of said bimorph means is mounted between said second end of said base and a second end of said brace, and
    at least a fifth one of said bimorph means is connected to said brace in an orientation perpendicular to said first and said second bimorph means; such that
    a user can control the direction of movement of said device along said first, second, and third axes by varying said electrical potential applied to said bimorphs.

3. The device of claim 2 wherein:
    each of said bimorph means comprises a first conductive element and a second conductive element, each said element is electrically isolated from said other element, and said means for applying an electrical potential to said bimorphs comprises a means for applying a first voltage of a first polarity to said first conductive element of said bimorph and a second voltage of a second polarity to said second conductive element of said bimorph.

4. The device of claim 3 wherein:
    at least one of said bimorph means comprises a third conductive element.

5. The device of claim 4 wherein:
    at least one of said bimorph means comprises a non-conductive band in a central region of an outer surface thereof, said non-conductive band divides said outer surface into two regions.

6. The device of claim 2 wherein:
    at least one of said bimorph means comprises a non-conductive band in a central region of an outer surface thereof, said non-conductive band divides said outer surface into two regions.

7. The device of claim 2 wherein:
    said device further includes a balance attachment, said balance attachment is adapted to measure forces that take a long time to reach equilibrium and forces that are very weak, said balance attachment comprising
    a balance arm supported by a cross-spring flexure pivot which ensures substantially frictionless rotation about a horizontal axis passing through a pivot point,
    at least two screws on said arm that are adjusted to ensure substantially zero restoring force on said balance attachment,
    at least two screws on a carrier to act as end-stops,
    a permanent, low hysteresis magnet is attached to a first end of said balance arm, and said lower surface is secured at a second end of said balance arm.

8. The device of claim 2 wherein:
    said device further includes means to measure lateral forces, said lateral forces measuring means comprising a plurality of miniature semi-conductor strain gauges attached to frictionless torsion wires, said strain gauges are employed in a two bridge configuration from which displacements along said first and said second axes can be independently measured.

9. The device of claim 1 wherein:
    said device further includes a balance attachment, said balance attachment is adapted to measure forces that take a long time to reach equilibrium and forces that are very weak, said balance attachment comprising a balance arm supported by a cross-spring flexure pivot which ensures substantially frictionless rotation about a horizontal axis passing through a pivot point, at least two screws on said arm that are adjusted to ensure substantially zero restoring force on said balance attachment, at least two screws on a carrier to act as end-stops, a permanent, low hysteresis magnet is attached to a first end of said balance arm, and said lower surface is secured at a second end of said balance arm.

10. The device of claim 1 wherein:

said device further includes means to measure lateral forces, said lateral forces measuring means comprising a plurality of miniature semi-conductor strain gauges attached to frictionless torsion wires, said strain gauges are employed in a two bridge configuration from which displacements along said first and said second axes can be independently measured.

* * * * *